United States Patent [19]  
Hamaguchi et al.

[11] Patent Number: 4,844,904  
[45] Date of Patent: Jul. 4, 1989

[54] LIPOSOME COMPOSITION
[75] Inventors: Naoru Hamaguchi, Ibaraki; Katsumi Iga, Suita; Yasuaki Ogawa, Ibaraki, all of Japan
[73] Assignee: Takeda Chemical Industries, Ltd., Osaka, Japan
[21] Appl. No.: 933,619
[22] Filed: Nov. 21, 1986
[30] Foreign Application Priority Data Nov. 22, 1985 [JP] Japan .................................. 262739

[51] Int. Cl.⁴ ...................... A61K 37/22; A61K 9/66; A61K 45/05; B01J 13/02
[52] U.S. Cl. .................................... 424/450; 264/4.3; 264/4.6; 424/7.1; 424/85.2; 424/94.3; 428/402.2; 436/829; 514/885
[58] Field of Search ................... 264/4.6; 428/402.2; 424/420, 450; 436/829

[56] References Cited  
U.S. PATENT DOCUMENTS

| | | | |
|---|---|---|---|
| 4,217,344 | 8/1980 | Vanlerberghe et al. | 428/402.2 X |
| 4,235,871 | 11/1980 | Papahadjopoulos et al. | 424/450 |
| 4,377,567 | 3/1983 | Geho | 424/450 X |
| 4,515,736 | 5/1985 | Deamer | 264/4.3 |
| 4,565,696 | 1/1986 | Heath et al. | 514/2 X |
| 4,594,241 | 6/1986 | Rao | 424/450 |
| 4,652,441 | 3/1987 | Okada et al. | 264/4.6 X |

FOREIGN PATENT DOCUMENTS 0072234 2/1983 European Pat. Off. .  
0126580 11/1984 European Pat. Off. .  
2157172 10/1985 United Kingdom .

OTHER PUBLICATIONS

Lenk et al., "Novel Multilayered Lipid Vesicles . . . ", Biochemistry, vol. 24, May 1985, pp. 2833-2842.  
Chem. Abstr., vol. 97 (1982), 35016q.  
Tsao et al., "Sendai Virus Induced Leakage of Liposomes Containing Gangliosides", Biochemistry, vol. 24, Feb. 1985, pp. 1092-1098.  
Lichtenberg et al., "Effect of Surface Curvature on Stability, . . . Single Lamellar Vesicles", Biochemistry, vol. 20, Jun. 1981, pp. 3462-3467.  
Chem., Abstr., vol. 100 (1984) 12523u.  
Chem. Abstr., vol. 94(1981), 162698b.  
Higgins et al., Journal of Pharmacy and Pharmacology, vol. 36, Supplement, 1984, p. 24P.

Primary Examiner—Richard D. Lovering  
Attorney, Agent, or Firm—Wenderoth, Lind & Ponack

[57] ABSTRACT

Liposome compositions in which a drug is retained in stable condition are prepared by dispersing liposomes obtained by removal of a solvent from a drug-containing w/o emulsion in an aqueous solution having an osmotic pressure higher by at least 20 percent than the osmotic pressure of a solution used for entrapping the drug in said liposomes. This composition is conducive to a sustained therapeutic efficacy or a better delivery of the drug to a target organ.

4 Claims, 3 Drawing Sheets

Osmotic pressure at preparation of liposomes/
osmotic pressure of physiological saline Osmotic pressure at preparation of liposomes/
osmotic pressure of physiological saline

LIPOSOME COMPOSITION

BACKGROUND OF THE INVENTION

The present invention relates to a liposome composition. More particularly, the present invention relates to a liposome composition in which a drug is retained in a stable condition within liposomes and which is conducive to a sustained therapeutic efficacy or a better delivery of the drug to a target organ.

In using liposomes as carriers for drugs, it is essential to improvement of therapeutic effects to ensure that the drugs are retained in as stable a condition as possible within the liposomes. Heretofore, much research has been undertaken into the stability of liposomes but little attention has been paid to the relationship between the stability of liposomes and the osmotic pressure in preparation. As mentioned in "Saibo Kogaku" (Cell Engineering)2, 1136 (1983), for instance, it has been claimed that "as a rule, it is essential that the solution in preparation is isotonic with the solution used later as the disperse medium". On the other hand, no attention has been paid to the case in which the solution in the preparation of liposomes is lower than the osmotic pressure used later as the dispersion medium.

SUMMARY OF THE INVENTION

In view of the above situation, the present inventors conducted an extensive study for developing a method that would allow a drug to be retained in stable condition within liposomes, particularly in relation to osmotic pressure, and established the present invention. Thus, the present invention is directed to a lipsome composition comprising liposomes obtained by removing a solvent from a drug-containing w/o emulsion and an aqueous disperse medium having an osmotic pressure higher by at least 20 percent than the osmotic pressure of the solution used for entrapping the drug in said lipsome. (Hereafter "the solution used for entrapping into liposomes" may be referred to as "the bulk solution".)

DETAILED DESCRIPTION OF THE INVENTION

Figure 1:
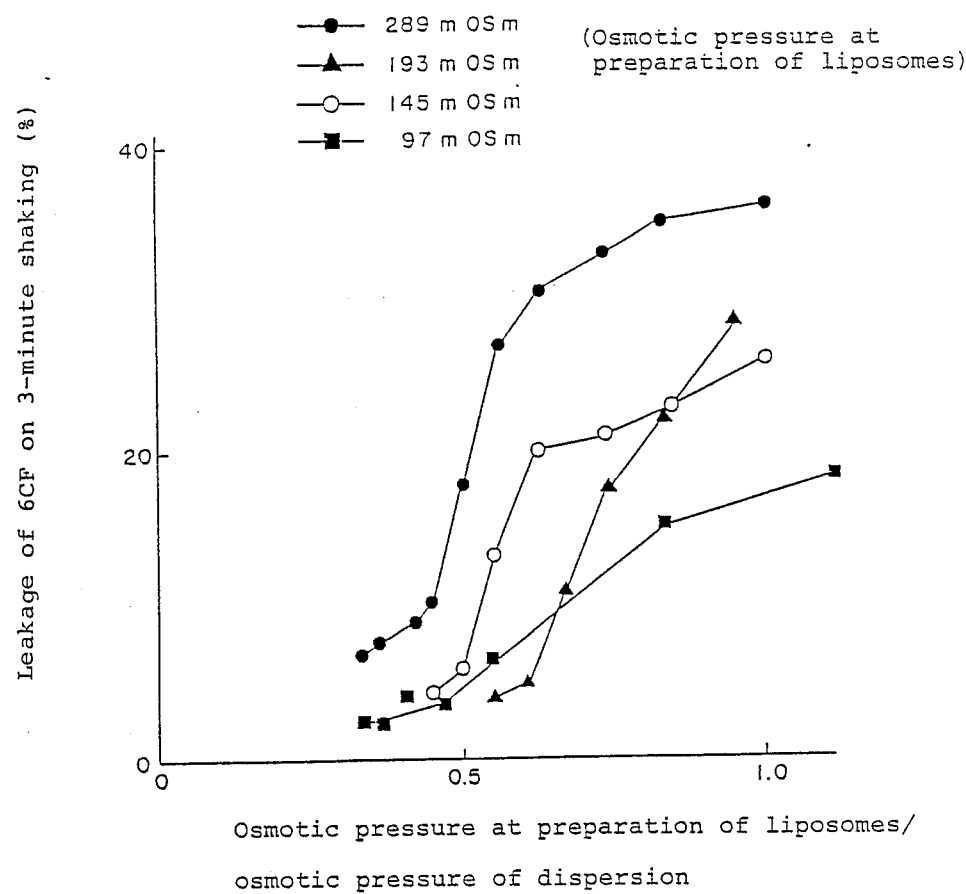
FIGS. 1-3 show the relationship between the amount of drug leakage from liposomes and osmotic pressure under different conditions.

The liposome composition according to the present invention can be prepared in the following manner.

The drug-containing w/o emulsion can be prepared by emulsifying a bulk solution with an organic solvent containing a phospholipid by a conventional procedure.

The phospholipid that can be used in accordance with the present invention may be one that is commonly used in the preparation of liposomes. For example, phospholipids derived from egg yolk, soybean or other vegetable or animal tissue, such as phosphatidylcholines, phosphatidylethanolamines, phosphatidic acid, phosphatidylserines, phosphatidylinositols, phosphatidylglycerols, sphingomyelins, etc.; mixtures thereof such as egg yolk phospholipid, soybean phospholipid, etc.; hydrogenation products thereof; and synthetic phospholipids such as dipalmitoylphosphatidlcholines, distearoylphosphatidylcholines or the like may be mentioned. These phospholipids may be used singly or as a mixture of two or more species. For stabilization of liposomes and other purposes, cholesterol, α-tocopherol, dicetyl phosphate, stearylamine or the like may be added.

The bulk solution is an aqueous solution prepared by dissolving appropriate water-soluble substances necessary for adjustment of osmotic pressure in water and, depending on the particular case, may be a mere aqueous solution of a drug. The water-soluble substances mentioned above include various buffers (for example, phosphate buffer, citrate buffer, etc.), various salts (for example, sodium chloride, monosodium phosphate, disodium phosphate, etc.), carbohydrates (for example, glucose, galactose, maltose, maltotriose, mannose, sorbitol, etc.), amino acids (for example, glycine etc.) and so on. These substances may be used singly or in admixture. In this bulk solution, there may be incorporated a preservative (for example, paraben, etc.) if necessary. The amount of said water-soluble substances to be dissolved is generally controlled so that the osmotic pressure of the bulk solution will be in the range of about 50 to 500 mOsm. The specific osmotic pressure to be used depends on the intended use of the liposome composition. For example, when the preparation is to be administered as an injection, an ophthalmic solution or a nasal preparation, the osmotic pressure is preferably adjusted to about 50 to 240 mOsm. For use as a diagnostic agent, there is no particular limitation on osmotic pressure.

Regarding the drug used in accordance with the present invention, it may be a hydrophilic drug or a lipophilic drug, or a mixture of them. Examples of such hydrophilic drug include various antiinflammatory analgesics, lymphokines, anticancer agents, immunopotentiators, physiologically active peptides, antibiotics, antiprotozoa agents, enzymes, antiallergic drugs and so on. Among said antiinflammatory analgesics are manganese superoxide dismutase (SOD), superoxide dismutase-PEG (SOD-PEG; the molecular weight of PEG=5000) (Japanese Patent Application Laid-open No. 58-16685 and European Patent Publication No. 0070656) which is a derivative of SOD, lipomodulins and so on. Among said lymphokines are natural or genetrically engineered interferons (α, β, γ) and natural or genetically engineered interleukin 2. Examples of said anticancer agents include adriamycin, actinomycin, 1-β-arabinofuranosylcytosine, bleomycin, cisplatin and so on. The immunopotentiators may for example be muramyl dipeptide, muramyl tripeptide, and so on. The physiologically active peptides include, among others, thyroid hormone releasing hormone (TRH), leuprolide, insulin, DN-1417 (Japanese Patent Application Laid-open No. 59-21613 and European Patent Publication No. 0094157) and so on. The antibiotics may be β-lactam antibiotics such as sulbenicillin, cefotiam, cefmenoxime, sulfazecin, etc., and aminoglycoside antibiotics such as gentamycin, streptomycin, kanamycin, etc., for instance. Examples of said antiprotozoa agents include antimony drugs such as meglumine antimonate and so on. Examples of said enzymes include alkali phosphatase, etc. And amoxanox can be mentioned as a representative of said antiallergic drugs.

As examples of said lipophilic drug, there may be mentioned anticancer agents such as ansamitocins, etc.; immunopotentiators such as TMD-66 [Gann (Cancer) 74 (2), 192-195 (1983)], MTP-PE [Japanese Patent Application Laid-open No. 59-163389 and Journal of Biological Response Modifiers, Vol 1, 43-55 (1982)], etc., and phospholipid derivatives (Japanese Patent Application Laid-open No. 59-163389).

In the preparaton of said emulsion, it is generally preferable to incorporate a hydrophilic drug in said bulk solution or a lipophilic drug in the organic solvent phase.

The organic solvent may be virtually any solvent in which said phospholipid can be dissolved. By way of example, chloroform, ethers (for example, diethyl ether, isopropyl ether, etc.), alcohols (for example, methanol, ethanol, etc.) may be used alone or as a mixture.

The production of liposomes from a w/o emulsion in the practice of the present invention can be performed generally in the manner described in Proceedings of the National Academy of the United States of America 75, 4194 (1978) or in accordance with the procedure described in Japanese Patent Laid-open No. 55-118415 and U.S. Pat. No. 4,235,871. The amount of the organic solvent used in the preparation of said emulsion is gnerally about 2 to 10 times the amount of the bulk solution. The amount of phospholipid is about 10 to 100 μmol per ml of the bulk solution and generally the phospholipid is preferably dissolved in the organic solvent beforehand. The amount of the drug is chosen in consideration of the amount necessary for development of drug efficacy, the dosing volume, and other factors.

The emulsification for obtaining said w/o emulsion can be achieved by the conventional techniques such as stirring, the pressure method, sonication, and so on. In the case of sonication, about 1 to 20 minutes of treatment with a 20 kHz probe results in a uniform emulsion.

From the w/o emulsion thus prepared, the solvent is removed by a routine technique. For example, the emulsion is put in an eggplant-shaped flask having a capacity of about 10 to 100 times the bulk solution volume and the solvent is distilled off on a rotary evaporator. The temperature for this operation is preferably higher by about 10° C. than the phase transition temperature of the phospholipid and it is preferable to conduct an initial phase of distillation at a reduced pressure of about 100 to 400 mmHg and, after the contents have formed gels, at a reduced pressure of about 60 to 700 mmHg. Further distillation yields REV (reverse-phase evaporation vesicle)-type liposomes. These liposomes have a unilamellar structure or an oligolamellar structure (usually, consisting of phospholipid bilayers of not more than about 10 lamellae) and contain the drug in them. The liposomes obtained by the above procedure are then dispersed in an aqueous phase of a disperse medium having an osmotic pressure higher by at least 20 percent than the bulk solution to give a liposome composition of the present invention. The osmotic pressure of this disperse medium is preferably higher by about 50 percent than the osmotic pressure of the bulk solution and, more desirably about 100 percent higher. This disperse medium can be prepared using suitable water-soluble substances selected from the substances used in the preparation of the bulk solution and these substances may be the same as or different from those used in the bulk solution. When the liposome composition is intended for application to the living body, the osmotic pressure of the disperse medium is preferably approximately isotonic with the body fluid and, therefore, a bulk solution having an osmotic pressure not more than about 80 percent of the osmotic pressure of body fluid is employed.

The liposome fluid obtained after removal of the solvent contains the drug in nonencapsulated form, as well as the drug which has been encapsulated in the liposomes, and the entire liposome fluid in this form can be added to the above disperse medium. In this case, an aqueous solution containing the water-soluble substances in higher concentration than the bulk solution or the substance itself may be added to adjust the final osmotic pressure of the disperse medium to the above-mentioned range.

On the other hand, when it is desired to remove the drug not entrapped into liposomes, this removal and the dispersion into a disperse medium specified according to the present invention can be simultaneously carried out. The methods for removal include dialysis, filtration (for example, gel filtration), centrifugation, and so on. In the case of dialysis, the liposomes are put in a dialysis bag and immersed in the above dispersion. By repeating this procedure, the liposome composition of the present invention can be obtained. In the case of gel filtration, the prepared liposome fluid is subjected to fractionation using the above disperse medium as the eluent and the liposome-containing fractions are recovered. In the case of centrifugation, the preparation liposome fluid is centrifuged and the precipitated portion is redispersed in the above disperse medium. Further, in removal of said nonencapsulated drug, one may remove the nonencapsulated drug under conditions isotonic with the core phase and immediately add the lipsomes to the above dispese medium.

The quantitative proportions of the disperse medium and liposomes are selected in consideration of the desired entrapping amount of the drug and the dose required for development of drug efficacy.

Since, in accordance with the present invention, the drug is stably entrapped within liposomes and the leakage of the drug is minimized during storage or under shaking, the liposomes according to the present invention can be used with advantage in practical applications. The liposome composition according to the present invention can be used for the administration of drugs having various therapeutic or other effects to the living body in such dosage forms as injections, eye drops, nasal drops, and so on and is of value for attaining enhanced therapeutic or other effects owing to the increased drug stability, prolongation of efficacy, improved organ targeting and other advantages. Furthermore, the invention provides highly stable preparations also in the case of diagnostic liposomal products utilizing antigen-antibody reactions, for instance.

The following experimental examples, test examples and working examples are further illustrative of the present invention. In the following description, the osmotic pressures are those measured by means of an Osmet ® (Precision Systems Inc.)

EXPERIMENTAL EXAMPLE 1

(1) to 0.02 m phosphate buffer (pH 7.2) was added 0.05 M 6-carboxyfluoroscein (Eastman Kodak; hereinafter referred to briefly as 6CF) followed by addition of sodium chloride to give a bulk solution with an osmotic pressure of 289 mOsm. A 5 ml portion of this solution was mixed with 5 ml of distilled water to give a bulk solution (145 mOsm). This bulk solution was added to a solution of 210 mg dipalmitoylphosphatidylcholine (DPPC) and 90 mg distearoylphosphatidylcholine (DSPC) in chloroform-isopropyl ether (20 ml/20 ml) and the mixture was subjected to six cycles of sonication (room temperature, 50W, 30 seconds) with an ultrasonic homogenizer (Ohtake Seisakusho K.K., 20 kHz)

to give a w/o emulsion. This emulsion was evaporated on a water bath in a rotary evaporator (55° C.) to remove the solvent, whereby REV type liposomes were obtained. The 6CF not entrapped in the liposomes were removed by dialysis against physiological saline (287 mOsm) using dialysis membrane tube (Spectrapor ®, Spectrum Medical Industries; cut-off molecular weight 6000-8000), and large vesicles were removed by means of a 5 μm filter (Acrodisc ®, Gelman). In this manner, a preparation comprising a saline dispersion of 6 CF-entrapping liposomes was obtained.

(2) The above procedure 1) was repeated except using a bulk solution (97 mOsm) prepared by mixing 5 ml of 0.05 M 6CF-0.02 M phosphate buffer (pH 7.2) (adjusted to 193 mOsm with sodium chloride) with 5 ml of distilled water to give a liposome composition.

(3) The procedure 1) was repeated except using 10 ml of 0.05 M 6CF-0.02 M phosphate buffer (pH 7.2) adjusted to 193 mOsm with NaCl as a bulk solution to give a liposome composition.

(4) The procedure 1) was repeated except using 10 ml of 0.05 M 6CF-0.02 M phosphate buffer (pH 7.2) adjusted to 289 mOsm with NaCl as a bulk solution to give a liposome composition.

TEST EXAMPLE 1

The retention of 6CF in each of the liposome compositions obtained in Experimental Example 1 was tested in the following manner.

TEST METHOD (1)

(1) A 0.1 ml aliquot of each liposome composition was diluted with 9.9 ml of 0.067 M phosphate buffered saline (ph 7.2, 284 mOsm), followed by gentle stirring (Fluid A).

(2) 0.2 ml portions of the above dilution were added to 9.8 ml portions of 0.067 M phosphate buffered saline with diffreent osmotic pressures (disperse media), followed by gentle stirring (Fluid B). The intensity of fluorescence of 6CF as determined with Hitachi F3000 fluoro-photometer (exciting wavelength 494 nm, measuring wavelength 515 nm) was expressed as FB.

(3) Then, 5 ml of Fluid B was taken into a polystyrene round-bottomed sedimentation tube and afer 3-minute shaking (Iwaki Shaker V-S), the intensity of fluorescence of 6CF was measured and expressed as FC.

(4) To 0.1 ml of Fluid A was added 0.1 ml of 0.02% Triton X-100 and the mixture was incubated on a water bath at 45° C. for 10 minutes to disrupt the liposomes. Then, 4.8 ml of 0.067 M phosphate buffer (ph 7.2) was added and mixed (Fluid T). The intensity of fluorescence of 6CF was expressed as FT.

In the above test, the amount of leakage of 6CF from the liposomes after 3 minutes of shaking was expressed as $(FC-FB)/FT \times 100$ (%).

FIG. 1 shows the amounts of 6CF leakage from the respective liposomes upon 3-minute shaking in dispersions having various osmotic pressures. It will be apparent from the figure that when the osmotic pressure of the bulk solution at liposome preparation is held lower than the osmotic pressure of the disperse medium, the amount of 6CF leakage is decreased and the stability of the preparation is improved.

Figure 2:
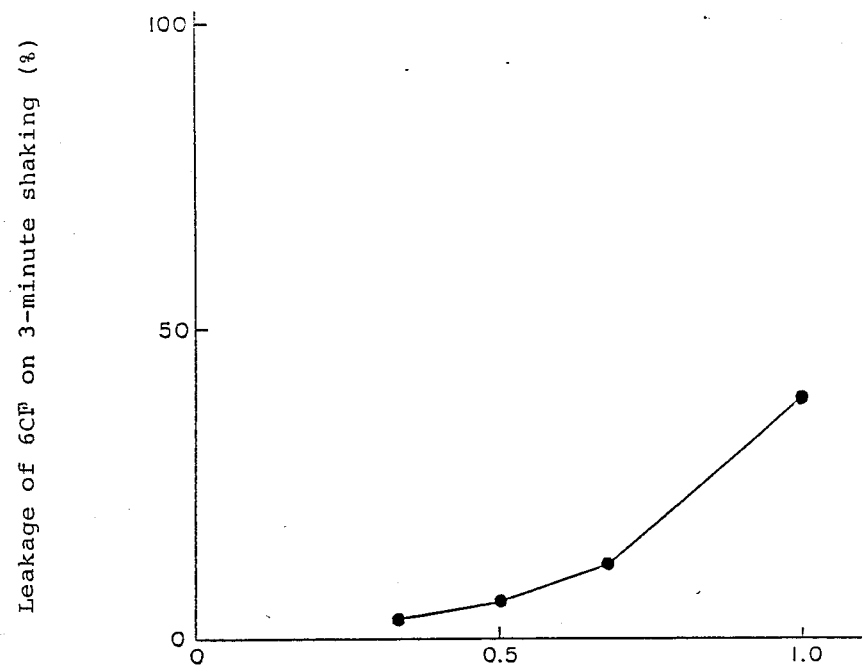

FIG. 2 shows the relationship between the amount of 6CF leakage on 3-minute shaking under conditions isotonic with biological fluid and the osmotic pressure of the bulk solution at preparation. It is found that when the osmotic pressure of the bulk solution at liposome preparation is lower than the osmotic pressure of the dispersion, the retention of the encapsulated drug is greater even under severe shaking conditions.

TEST METHOD (2)

Each of the above liposome preparations (Fluid B and Fluid T) was put in a polystyrene round-bottomed sedimentation tube, which was wrapped around with aluminum foil for protection against light and allowed to remain at room temperature for 4 days. Then, the intensity of 6CF fluorescence was measured. The intensities of fluorescence thus measured were taken as FB' and FT', respectively. The amounts of 6CF leakage (%) during the 4-day period were determined by means of the following equation:

$$(FB/FT-FB'/FT') \times 100 \text{ (\%)}$$

Figure 3:
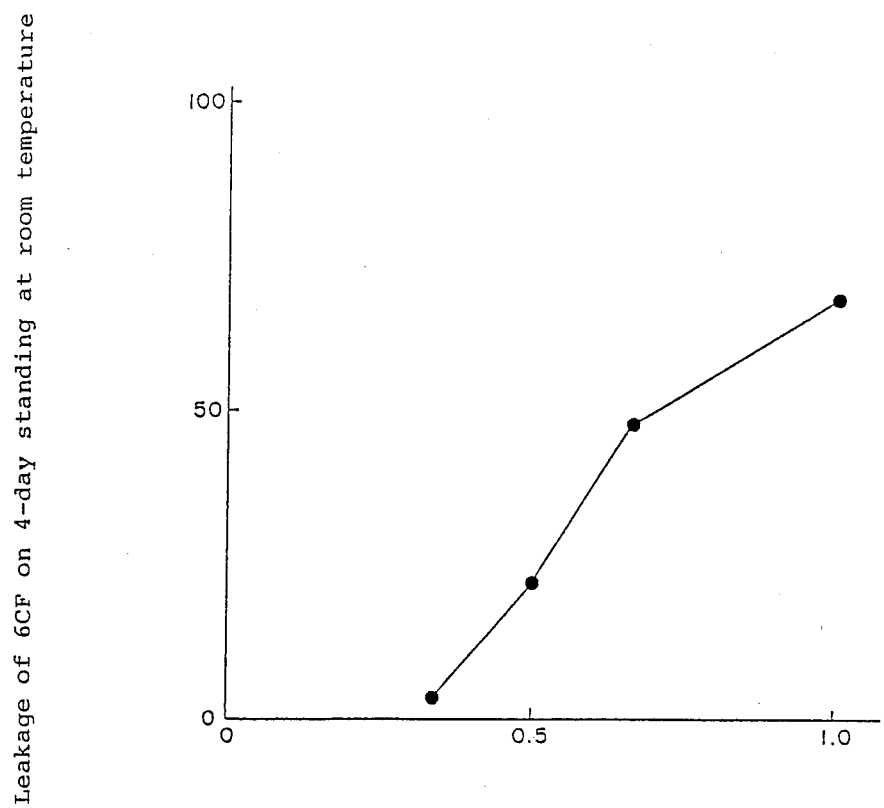

The test results are shown in FIG. 3. It is apparent from the figure that in the case of 4-day standing at room temperature, too, the low osmotic pressure of the bulk solution at liposome preparation relative to the osmotic pressure of the dispersion results in a reduced amount of 6CF leakage and a higher stability of the preparation.

TEST EXAMPLE 2

(1) Using a mixture (150 mOsm) composed of 5 ml of 0.05 M 6CF-0.02 M phosphate buffered saline (ph 7.2; 289 mOsm) and 5 ml of distilled water as a core aqueous phase and a solution of 300 mg of egg yolk phosphatidylcholine (Sigma, P2772) in chloroform-isopropyl ether (20 ml/20 ml), REV liposomes were prepared in the same manner as Experimental Example 1-1).

(2) The above procedure (1) was repeated except using a mixture (287 mOsm) of 5 ml of 0.05 M 6CF-0.02 M phosphate buffered saline (ph 7.2; 289 mOsm) and 5 ml of 0.067 M phosphate buffered saline (pH 7.2; 284 mOsm) to give a liposome composition (control).

Each of the liposome compositions obtained in (1) and (2) was subjected to the following test. Thus, 0.1 ml of each liposome compositions was added to 9.9 ml of phosphate buffered saline (pH 7.2; 284 mOsm) and after gentle mixing, a 2 ml portion was put in a Sartorius dialyzer [Centrisart I; cut-off molecular weight 20,000) and centrifugated at 3000 rpm for 15 minutes (Hitachi 05PR-22 centrifuge) to give a liposome-free liquid. A 0.1 ml portion of this liquid was added to 4.9 ml of 0.067 M phosphate buffered saline in a polystyrene round-bottomed sedimentation tube and, after gentle mixing, the intensity of fluorescence FO was measured. Separately, 0.1 ml of Fluid (A) was layered on 4.9 ml of 0.067 M phosphate buffered saline (pH 7.2) in a 10 ml sedimentation tube and the tube was inverted 3 times for mixing (Fluid B).

The intensity of fluorescence was measured and expressed as FB. On the other hand, 0.1 ml of Fluid (A) was subjected to the above-mentioned Triton X-100 treatment and the intensity of fluorescence was measured and expressed as FT. The leakage of 6CF (%) due to dilution of Fluid (B) was expressed by the formula $(FB-FO)/FT \times 100$ (%).

The amounts of 6CF leakage due to dilution of the above liposome compositions (1) and (2) were 7.7% and 24.5%, respectively.

EXAMPLE 1

(1) A mixed aqueous solution (148 mOsm) composed of 5 ml of 0.067 M phosphate buffered saline (pH 7.2, 287 mOsm) containing 25 mg of manganese SOD-PEG (5000) and 5 ml of distilled water was mixed with a solution of 30 mg DSPC and 270 mg DPPC in chloroform-isopropyl ether (30 ml/30 ml) and the mixture was sonicated with an ultrasonic homogenizer (50W, 30 seconds) for a total of 6 cycles to give an emulsion. Then, using a rotary evaporator, the solvent was removed on a water bath at 55° C. to give REV liposomes. After separation by high speed centrifugation (50,000 g 20 min., Sorval), 0.067 M phosphates buffered saline (pH 7.2; 287 mOsm) was added for dispersion. The centrifugation was repeated twice and large liposome vesicles were removed with a 5 μm Acrodisc ® filter. In this manner, a REV liposome composition having SOD-PEG (5000) entrapped in stable condition was obtained.

(2) The above procedure was repeated except using 10 ml of 0.067 M phosphate buffered saline (pH 7.2; 288 mOsm) containing 25 mg of manganese SOD-PEG (5000) to give liposomes. The liposomes were dispesed in a similar disperse medium to give a liposome preparation (control).

Each of the above liposome composition was subjected to the following test.

In a polystyrene round-bottomed sedimentation tube, 0.2 ml of 0.02% Triton X-100 was added to 0.1 ml of the above liposome composition. After the mixture was allowed to stand in a water bath at 50° C. for 10 minutes, 4.7 ml of a 2.6% aqueous solution of sodium borate was added (Fluid T). Separately, 0.2 ml of each liposome compositions was taken and gently mixed with 9.8 ml of a 2.6% aqueous solution of sodium borate. This mixture was divided into halves and put in polystyrene round-bottomed sedimentation tubes. One of the tubes was allowed to stand at room temperature (Fluid B) and the other in a water bath at 50° C. (Fluid W). Each of Fluids T, B and W and a blank 2.6% aqueous solution of sodium borate (Fluid BL) was transferred to a 10 ml centrifuge tube of PYREX glass, where under sufficient stirring 0.1 ml of a solution of fluoroescamine in acetone (Roche, Fluram "Roche", 1 mg/ml) was added and the intensity of fluorescence (F) was measured at an excitation wavelength of 390 nm and a measuring wavelength of 475 nm. The leakage (%) of manganese- SOD-PEG (5000) due to the 5-minute immersion at 50° C. was calculated by means of the following equation.

Leakage of manganese-SOD-PEG (5000)

$$=(FW-FB)/FT-FBL\times 100\ (\%)$$

Thus, the amounts of leakage of SOD-PEG (5000) from the above liposome compositions obtained in (1) and (2) upon 5-minute incubation in a water bath at 50° C. were 2.7% and 25.4%, respectively. It is, thus, clear that the liposome composition according to the present invention is superior in stability.

EXAMPLE 2

(1) The procedure of Example 1-1) was followed using a mixed aqueous solution (147 mOsm) composed of 5 ml of 0.067 M phosphate buffered saline containing 30 mg of manganese-SOD (pH 7.2, 289 mOsm) and 5 ml of distilled water to give a liposome composition.

(2) The above procedure (1) was repeated except that liposomes were prepared using 10 ml of 0.067 M phosphate buffered saline (pH 7.2; 289 mOsm). The resulting liposome preparation was used as a control.

The amounts of leakage from the above liposome compositions (1) and (2) upon 5-minute immersion in a water bath at 50° C. in the manner described in Example 1 were 9.6% and 86.0%, respectively.

EXAMPLE 3

(1) The procedure of Example (1-1) was followed using a mixture of 5 ml of an injection containing 2.5 mg of CDDP (cisplatin) (Nippon Kayaku, Randa Inj., Japan) and 5 ml of distilled water and a phospholipid solution (DSPC/DPPC=30 mg/270 mg; chloroform-isopropyl ether=30 ml/30 ml) to give a liposome composition.

(2) The procedure of Example (1-1) was followed using a mixture of 5 ml of a CDDP injection (2.5 mg, Randa Inj., Nippon Kayaku) and 5 ml of physiological saline for injection (Otsuka Pharmaceutical, 284 mOsm) to give a liposome composition (control).

Each of the above liposome compositions (1) and (2) (0.5 ml) was added to 9.5 ml of physiological saline (287 mOsm) and stirred gently (Fluid A). A 0.2 ml portion of Fluid A was taken and gently mixed with 9.8 ml of physiological saline (287 mOsm). The mixture was divided into halves and put in polystyrene roundbottomed sedimentation tubes. One of the tubes was allowed to stand at room temperature (Fluid B) and the other tube was shaken at room temperature for 3 minutes (Fluid C). Separately, 0.1 ml of Fluid A was mixed with 0.1 ml of 0.02% Triton X-100 and the mixture was incubated (45° C., 10 minutes). It was mixed with 4.8 ml of physiological saline to give a fluid containing disrupted liposomes (Fluid T). The amounts of CDDP leaked from the liposomes of Fluids B, C and T were determined by adduct formation with diethyl dithiocarbamate and subsequent HPLC (column: Zorbax CN ®; eluent: n-hexane-isopropyl alcohol=8:2 V/V; 254 nm). The results were expressed as H. The, the leakages of CDPP from liposomes on 3-minute shaking were calculated by means of the equation:

$$(Hc-Hb)/Ht\times 100\ (\%).$$

The leakage of CDDP from liposomes during 3 minutes of shaking were 6.4% and 82.7%, respectively. It was thus clear that the low osmotic pressure of the bulk solution relative to the osmotic pressure of the disperse medium helps stabilize the liposomes.

EXAMPLE 4

Using an aqueous solution of a α-interferon, water and sodium chloride, there was prepared 10 ml of an aqueous solution of 200 μg protein/ml having an osmotic pressure of 143 mOsm. Then, using this solution, a w/o emulsion was prepared in the same manner as Example (1-1). Removal of the solvent gave REV liposomes. Large visicles were removed by filtration through a 5 μm Acrodisc ® filter and the residue was dialyzed against physiological saline using a dialysis membrane (Spectropor ®, cut-off molecular weight 25000) to remove the nonencapsulated drug. The above procedure gave a stable α-interferon-containing liposome composition having a hypotonic core or internal phase.

EXAMPLE 5

Using an aqueous solution of interleukin 2, water and sodium chloride, there was prepared an aqueous solution of 308 μg protein/ml having an osmotic pressure of 143 mOsm. A 5 ml portion of this aqueous solution was added to an organic solvent solution of egg yolk phosphatidylcholine (150 mg in 15 ml chloroform-15 ml isopropyl ether) in a 100 ml eggplant-shaped flask to prepare a w/o emulsion in the same manner as Example (1-1). Removal of the solvent gave REV liposomes. This preparation was centrifuged (50000 g, 20 min.) and redispersed in 5 ml of physiological saline. The centrifugation and redispersion were repeated, followed by filtration through a 5 μm Spectropor ® filter. The above procedure gave a liposome composition containing interleukin 2 stably encapsulated.

What we claim is:

1. A liposome composition comprising (1) REV liposomes obtained by removing a solvent from a drug-containing w/o emulsion, said emulsion being obtained by emulsifying a solution used for entrapping the drug in liposomes with a chloroform-isopropyl ether solution containing dipalmitoylphosphatidylcholine and distearoylphosphatidylcholine, wherein said solution used for entrapping the drug in the liposomes has an osmotic pressure of about 50 to 240 mOsm, and said drug is one selected from the group consisting of crisplatin, interleukin 2, manganese superoxide dismutase and superoxide dismutase-PEG, and (2) and aqueous disperse medium having an osmotic pressure which is about isotonic with the body fluid.

2. The composition according to claim 1, wherein the drug is interleukin 2.

3. The composition according to claim 1, wherein the drug is cisplatin.

4. The composition according to claim 1, wherein the drug is manganese superoxide dismutase or superoxide dismutase-PEG.

* * * * *